United States Patent [19]

Le Nouvel et al.

[11] Patent Number: 5,097,706

[45] Date of Patent: Mar. 24, 1992

[54] DEVICE FOR TAKING THE MEASUREMENTS OF THE VARIOUS COMPONENT ELEMENTS OF THE MOVEMENT OF A MOVING BODY

[75] Inventors: Alain Le Nouvel, Les Brevieres; Thierry Dronka, Creteil; Andre Maginot, Champigny Sur Marne; Michel Daveine; Jean-Louis Jouffroy, both of Paris, all of France

[73] Assignee: Association Persival, Saumur, France

[21] Appl. No.: 534,704

[22] Filed: Jun. 6, 1990

[30] Foreign Application Priority Data

Jun. 9, 1989 [FR] France ................. 89 07641

[51] Int. Cl.⁵ .............................................. G01P 15/08
[52] U.S. Cl. ...................................... 73/493; 73/510; 73/865.4
[58] Field of Search ................... 73/493, 510, 865.4, 73/866.4; 119/29; 340/573; 364/566, 578

[56] References Cited

U.S. PATENT DOCUMENTS 3,955,562  5/1976  Farrar, Jr. .
4,190,968  3/1980  Clapp et al. .................. 119/29
4,601,206  7/1986  Watson ........................ 73/510
4,935,887  6/1990  Abdalah et al. ............... 364/566

FOREIGN PATENT DOCUMENTS 0296023    6/1988  European Pat. Off. .
3306813A1  2/1983  Fed. Rep. of Germany .
WO81/01507 6/1981  World Int. Prop. O. .

Primary Examiner—John E. Chapman
Attorney, Agent, or Firm—Darby & Darby

[57] ABSTRACT

A device for taking measurements of the various component elements of the movement of a moving body includes a support having an arch with two branches so as to straddle, for example, the withers of a horse. The support has a high point and two low points, symmetrical relative to the longitudinal median plane of the support. The support carries six accelerometers of which, in use, three are disposed so that their axes are parallel to a longitudinal axis X, two are disposed so that their axes are parallel to a vertical axis Z, and one accelerometer is disposed so that its axis is parallel to the transverse axis Y.

11 Claims, 1 Drawing Sheet

DEVICE FOR TAKING THE MEASUREMENTS OF THE VARIOUS COMPONENT ELEMENTS OF THE MOVEMENT OF A MOVING BODY

BACKGROUND OF THE INVENTION

In French patent application No. 87.08050 filed on June 10, 1987 and published under No. 2,616,337 (corresponding to U.S. Pat. No. 4,935,887, issued June 19, 1990), a process is described whereby curves of the variations of the different components of the movement of a horse can be traced and reconstructed in a simulator.

According to this process, measuring means such as accelerometers and gyrometers are placed on a horse in real motion, or also an inertial control unit. With these instruments, the speeds of linear displacement along the three axes X, Y and Z as well as the rotational displacements about these axes are measured.

To perform this process, at first an inertial unit of the type used in airplanes, was attached on the saddle of a horse, and to this inertial unit a magnetic recording device was coupled. Such equipment soon proved to be unsatisfactory. In fact, such relatively heavy and bulky equipment excludes the presence of a rider so that the horse is left to itself and one is obliged to prod it to record the various gaits (walk, trot, gallop, jump). Therefore, such measurements give only indications relating to a circular course or represent only short straight lines. Besides, unavoidably, the center of gravity of such rather voluminous equipment is located too high above the horse's back; this falsifies the acceleration measurements and makes it necessary to introduce error correction calculations, which are only approximations. Lastly, because this equipment is heavy and fastened above the saddle, it is difficult to prevent the equipment from being subjected to parasitic motions due to swinging, and this, too, falsifies the measurements and is very complicated to correct.

It has been proposed, therefore, to use a metallic oversaddle, that is, a metal part shaped so that it exactly matches the form of a classic leather saddle; and on this oversaddle has been welded a metal platform carrying three gyrometers, and three accelerometers.

Thus, it has been possible to eliminate practically all parasitic movements of the measuring means; but, although the center of gravity of this equipment has been lowered, it is still some twelve centimeters above the horse's back. Of greatest importance, as before, the horse was still without a rider.

SUMMARY OF THE INVENTION

The present invention concerns a device able to eliminate all of the aforesaid disadvantages.

This device is a support piece having an arched form with two branches so as to have a median high point and two low points, symmetrical relative to the median plane of the support. An inner portion of this arched piece has a profile analogous to the cross-section of the withers of a horse. This support carries six accelerometers, three disposed along axes parallel to the longitudinal axis X, two disposed along axes parallel to the vertical axis Z, and one disposed along the transverse axis Y.

Preferably, this support is fastened to the saddle bow just before said bow, so that the point of convergence of the axis of symmetry of the support and the transverse axis Y is situated at the level of the horse's withers.

Thus, very light equipment of less than 2 kg is obtained, the equipment having practically no offset of the measuring means relative to the horse's withers, and allowing the horse to be mounted by its rider who, himself, carries on his back the recording system.

BRIEF DESCRIPTION OF THE DRAWINGS

The present invention has been represented in the annexed drawings by way of a non-limiting example.

DESCRIPTION OF THE PREFERRED EMBODIMENTS

Figure 1:
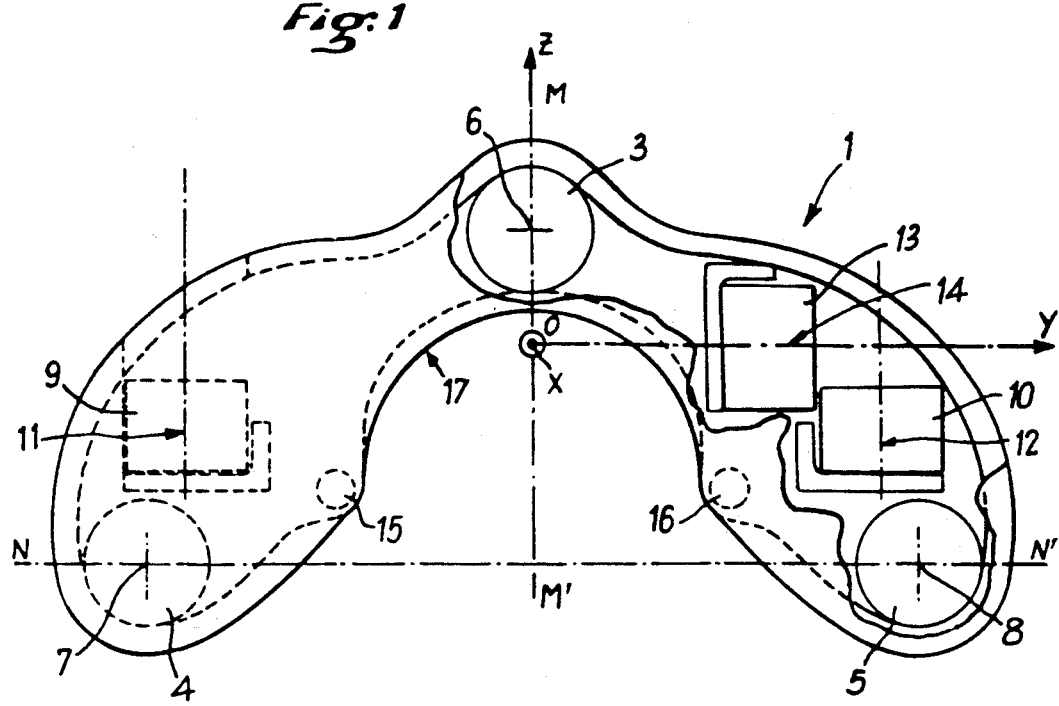
FIG. 1 is a front view of the support.

Referring to FIG. 1, the device includes a support or housing 1 having the general form of an arch or of an inverted rounded V, so as to present a high point situated on the plane of symmetry MM' and two low points, symmetrical relative to said plane MM'.

At the high point, an accelerometer 3 is placed whose axis 6 is parallel to the longitudinal axis X. At the low points, two accelerometers 4 and 5 are placed whose respective axes 7 and 8 are, likewise, parallel to said axis X and situated in a horizontal plane NN', perpendicular to the plane MM'.

In the vicinity of the accelerometers 4 and 5, two other accelerometers 9 and 10 are disposed. These two accelerometers are symmetrical relative to the plane of symmetry MM' And on the other hand, their respective axes 11 and 12 are parallel to the vertical axis Z.

On one of the two branches of the support 1 is disposed a sixth and last accelerometer 13, whose axis 14 is parallel to the transverse horizontal axis Y, perpendicular to the plane of symmetry MM'.

In the example shown, the six accelerometers 3, 4, 5, 9, 10, 13 are in cylindrical housings approximately 3 cm in diameter and 3 cm long.

Figure 2:
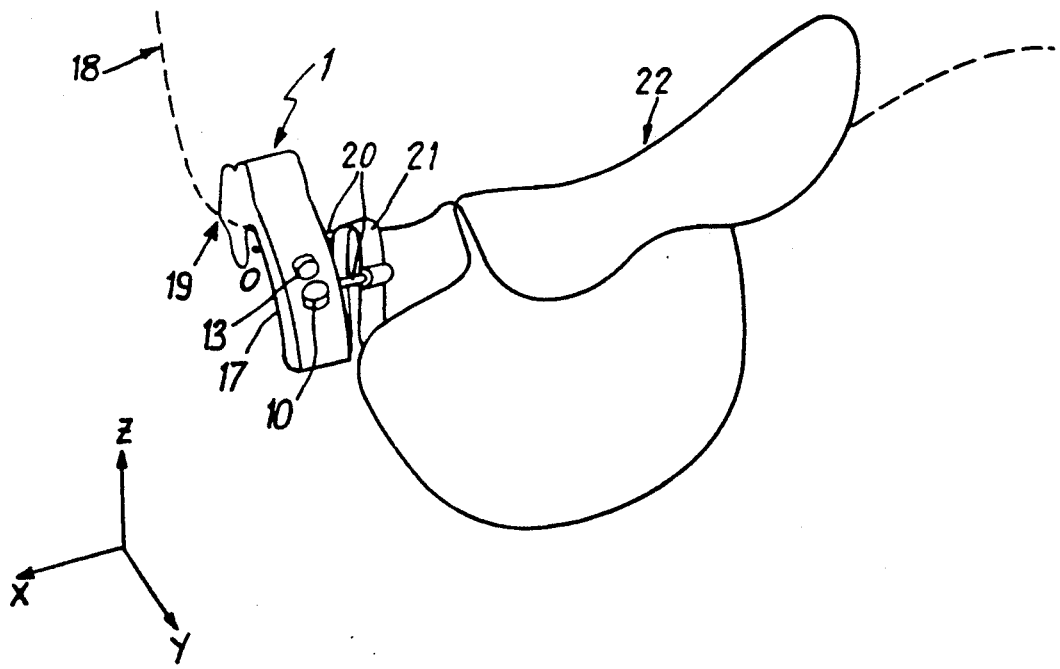
FIG. 2 is a perspective view of the support, according to the invention, mounted on a saddle.

Further, the support 1 has two fastening openings 15 and 16, symmetrical relative to the plane MM', which are preferably slightly conical and intended to receive two fastening fingers 20 carried by a metal piece 21 integral with the bow of a saddle 22 (FIG. 2). The device permits fast disassembly and reassembly in an identical position relative to the saddle.

In FIG. 2, there has been represented schematically by a dashed line 18, the body of the horse carrying the saddle 22, the withers being indicated at 19. It is illustrated that the inner contour 17 of the support 1 is defined so as to straddle the withers 19 of the horse. It is also illustrated that the axis 14 of the accelerometer 13 intersects at a point 0 the plane of symmetry MM', the form of the support 1 and the position of said axis 14 being determined so that said point 0 is, as represented in FIGS. 1 and 2, at the level of the horse's withers 19. The orientation of the axes X and Z can be inclined in the plane symmetry MM' to disengage the neck and to become adapted to the saddle.

The operation of the device thus described is the following.

The linear displacements are measured along the X axis through the three accelerometers 3, 4 and 5. One calculates the linear acceleration at point 0, by means of coefficients resulting from the geometry of the mount from measurements by the accelerometers 3, 4 and 5. Along the Z axis, one obtains the acceleration at point 0 by the average of the measurements of the two accelerometers 9 and 10, and along the Y axis by the measurement furnished by the accelerometer 13.

For the rotations, no gyrometers are available, but only accelerometers. The measurement of the rotation about the Z or yaw axis is obtained by the differential between the two accelerometers 4 and 5. The measurement of the rotation about the Y or pitch axis is obtained by the differential between the measurement derived from the accelerometer 3 and the average of the measurements deriving from the two accelerometers 4 and 5. The measurement of the rotation about the X or roll axis is given by the differential between the measurements furnished by the two accelerometers 9 and 10, these calculations furnishing the angular accelerations.

Thus, measurements of excellent precision are obtained whereas this was not possible with prior devices because of the multiplicity of the corrective calculations, which had to be introduced. The measurements are taken with much less bulky means that are much lighter, much simpler, and more reliable, as it is no longer necessary to have gyrometers. Lastly, this device permits the presence of a rider on the saddle 22 and, hence, guiding the horse as desired and making it execute the different gaits and figures under natural conditions, is possible.

In an example, which was made for purposes of experimentation, the width of the support 1 was 30 cm, its height 16 cm, its thickness 8 cm and its weight 2 kg. The various accelerometers 3, 4, 5, 9, 10 and 13 were connected to a multiple contact plug, which is not represented in the figures, and is located at the end of a multiconductor cable of a length of approximately twenty centimeters. The rider carries on his back the recording means which are connected to said plug. The rider or the horse carries the power supply batteries. The load carried by the rider was on the order of 8 kg.

Without going outside the scope of the invention, the recording and power supply means could be carried by a person moving alongside the horse.

The present invention has been described in connection with the study of the movement of a horse, the device being fastened to a saddle bow. But it must be understood that that is only one example of utilization, which is not limiting. In fact, this device may be employed for measurements of the various component elements of movement of any moving body whatsoever.

What is claimed is:

1. Device for taking measurements relative to longitudinal X, transverse Y and vertical Z axes of the various component elements of the movement of a moving body, comprising, a support having an arch form with two branches able to straddle a selected portion of said body, said support including a high point and two low points, symmetrical relative to the longitudinal median plane of said support; six accelerometers carried by said support, in use three said accelerometers being disposed with their axes parallel to the longitudinal axis X, two accelerometers disposed with their axes parallel to the vertical axis Z and one accelerometer disposed with its axis parallel to the transverse axis Y.

2. Device according to claim 1, wherein said accelerometers are connected to provide measurements of linear acceleration taken: along the X axis by means of the measurements from the three accelerometers having axes parallel to the X axis; along the Z axis by means of the measurements from the two accelerometers having axes parallel to said Z axis; along the Y axis by the measurement from the accelerometer having its axis parallel to said Y axis; and measurements of rotational accelerations taken: about the vertical axis Z by the differential of the measurements from two said accelerometers with axes parallel to the X axis; about the axis Y by the measurement differential between the average of said two accelerometers with axes parallel to the X axis and the third accelerometer with its axis parallel to the X axis; and about the axis X by the differential of the measurements from the two accelerometers with axes parallel to the Z axis.

3. Device according to claim 2, and further comprising means for integrating the measurements of angular and linear accelerations carried out along three orthogonal axes, to obtain the speeds and angular and linear displacements with respect to one point on said body.

4. Device according to claim 1, wherein the intended moving body is a horse, the inner portion of the support having a profile approximately corresponding to the contour of the body of a horse at the level of the withers, the device being dimensioned for fastening to the bow of a saddle with the point of intersection of said longitudinal median plane of the support and the axis of the transverse accelerometer having its axis parallel to the Y axis, is situated at the level of the horse's withers.

5. Device according to claim 4, wherein the support includes two fastening openings into which, in use, two fingers, carried by a metallic piece integral with the bow of a saddle, preferably near the strap or on a surcingle penetrate.

6. Device according to claim 4 and further comprising a source of electric energy and recording means to which said accelerometers are connected, said source and recording means being subject to carriage by at least one of the rider, the horse, and a person moving alongside the horse.

7. Device according to claim 3, in which the intended moving body is a horse and said point is a point at the level of the withers.

8. Device according to claim 2, wherein the intended moving body is a horse, the inner portion of the support having a profile approximately corresponding to the contour of the body of a horse at the level of the withers, the device being dimensioned for fastening to the bow of a saddle with the point of intersection of said longitudinal median plane of the support and the axis of the transverse accelerometer having its axis parallel to the Y axis, is situated at the level of the horse's withers.

9. Device according to claim 3, wherein the intended moving body is a horse, the inner portion of the support having a profile approximately corresponding to the contour of the body of a horse at the level of the withers, the device being dimensioned for fastening to the bow of a saddle with the point of intersection of said longitudinal median plane of the support and the axis of the transverse accelerometer having its axis parallel to the Y axis, is situated at the level of the horse's withers.

10. Device according to claim 5 and further comprising a source of electric energy and recording means to which said accelerometers are connected, said source and recording means being subject to carriage by at least one of the rider, the horse, and a person moving alongside the horse.

11. A device according to claim 1 in combination with a saddle, wherein said support includes two fastening openings, and said saddle includes a metal piece integral with the bow of said saddle, and two fingers carried by said metallic piece, in use, said metal fingers penetrating said openings to join said device with said saddle.

* * * * *